United States Patent
Pohan et al.

(10) Patent No.: US 6,925,142 B2
(45) Date of Patent: Aug. 2, 2005

(54) COMPUTER TOMOGRAPHY DETECTOR MODULE, DETECTOR FORMED THEREFROM, AND OPERATING METHOD

(75) Inventors: Claus Pohan, Baiersdorf (DE); Helmut Winkelmann, Eggolsheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/199,276

(22) Filed: Jul. 19, 2002

(65) Prior Publication Data

US 2003/0016779 A1 Jan. 23, 2003

(30) Foreign Application Priority Data

Jul. 19, 2001 (DE) .......................................... 101 35 288
Aug. 8, 2001 (DE) .......................................... 101 38 913

(51) Int. Cl.[7] .............................................. G21K 1/12
(52) U.S. Cl. .................... 378/19; 378/98.8; 250/370.15
(58) Field of Search ............................. 378/4, 19, 98.8; 250/370.09, 370.15

(56) References Cited

U.S. PATENT DOCUMENTS

| | | | | |
|---|---|---|---|---|
| 4,150,280 A | * | 4/1979 | Hurko ................... | 219/455.12 |
| 5,012,498 A | * | 4/1991 | Cuzin et al. ................... | 378/22 |
| 5,041,727 A | * | 8/1991 | Kojima et al. .............. | 250/352 |
| 5,248,885 A | * | 9/1993 | Sato et al. ............. | 250/370.15 |
| 5,444,752 A | * | 8/1995 | Dobbs et al. .................. | 378/19 |
| 5,841,828 A | * | 11/1998 | Gordon et al. ................. | 378/4 |
| 6,249,563 B1 | * | 6/2001 | Snyder et al. ................ | 378/19 |
| 6,327,330 B1 | * | 12/2001 | Peter ........................... | 378/19 |
| 6,497,511 B1 | * | 12/2002 | Schmitt et al. ............. | 378/207 |
| 6,667,482 B2 | * | 12/2003 | Von Der Haar ........ | 250/370.11 |

FOREIGN PATENT DOCUMENTS

JP  404110691 A  *  4/1992  ............ 250/370.15

\* cited by examiner

*Primary Examiner*—Craig E. Church
*Assistant Examiner*—Irakli Kiknadze
(74) *Attorney, Agent, or Firm*—Schiff Hardin LLP

(57) ABSTRACT

A detector module for an X-ray computed tomography apparatus has a sensor array composed of a number of sensor elements that is mounted on a front side of a printed circuit board. In order to enhance the precision of the detector, at least one heating element for heating the sensor array is provided at the backside of the printed circuit board facing away from the sensor array.

16 Claims, 4 Drawing Sheets

COMPUTER TOMOGRAPHY DETECTOR MODULE, DETECTOR FORMED THEREFROM, AND OPERATING METHOD

BACKGROUND OF THE INVENTION

1. Field of the Invention

The present invention is directed to a detector module for use in a computed tomography apparatus, as well as to an overall detector formed from a number of such detector modules, as well as to a method for operating a computed tomography apparatus.

2. Description of the Prior Art

German OS 195 02 574 discloses a detector with a number of parallel detector lines that proceed in the direction of the axis of a subject to be transirradiated, for example of a patient. A plurality of detector lines can be implemented as an assembly unit or a detector module. A sensor array formed of a number of such sensor elements is thereby accepted on a printed circuit board. The printed circuit board is connected via a flexible section to a further printed circuit board on which a plug is mounted for connection to evaluation electronics.

The sensor elements exhibit slightly different properties. It is necessary to calibrate each sensor element in order to avoid image artifacts. Calibration tables can be produced for this purpose with the assistance of special measuring devices. The calibration tables contain, for example, information about the temperature behavior, the radiation drift behavior, the relative signal strength, the afterglow, the location dependency of the signal strength, the spectral behavior or malfunctioning sensor elements.

The production of such calibration tables is extremely time-consuming and cost-intensive. Among the tasks required for this purpose are introduction of the detector modules into a special heating device and to subsequently determining the corresponding calibration data at prescribed temperatures.

Another possibility for avoiding image artifacts to the detector at a constant temperature by means of a heating device. U.S. Pat. No. 5,799,057 discloses a detector wherein the detector housing can be heated with a heating device. The detector housing usually exhibits a temperature elimination characteristic that is not uniform. A constant temperature over all sensor elements thus cannot be guaranteed. Given outage of one or more sensor elements, the entire detector must be replaced.

SUMMARY OF THE INVENTION

An object of the invention is to provide a detector or module wherein known sensor elements are avoided. In particular, it is an object to provide such a detector module with improved quality which can be manufactured economically.

This object is inventively in a detector module having a sensor array mounted on a printed circuit board and having at least one heating element for heating the sensor array disposed at the backside of the printed circuit board facing away from the sensor array. A detector having the multiple detector modules of this type, that can be heated independently of one another, can be repaired in a simple way. A failure or outage of the heating of all sensor arrays can no longer occur. A detector with the inventive detector modules can still deliver usable images when the heating of one of the detector modules has failed. Further, it is possible to compensate different localized heat elimination characteristics at the detector housing by means of the individual regulation of the heating elements of the detector modules.

In an advantageous embodiment, the heating element can be mounted lying opposite the sensor array, preferably on the printed circuit board. This enables an especially efficient heat transmission onto the sensor array.

Advantageously, regulating electronics arranged in the proximity of the heating elements are attached for regulating the heating element. If the heating element is arranged such that it co-heats the regulating element for regulating the heating element, the temperature dependency of the regulating electronics is compensated. The temperature of the sensor array can be held exactly in a prescribed, narrow temperature interval with the inventive detector module.

The regulating electronics preferably are fashioned as an integrated circuit. A temperature sensor can be applied on the printed circuit board. Expediently, the temperature sensor is a component of the regulating electronics. Preferably, the regulating electronics are arranged opposite the heating element at the side thereof facing away from the printed circuit board. This results in the heat output by the heating element being uniformly transmitted onto the regulating electronics, and the regulating electronics are always held at the same temperature.

Advantageously, the heating element is a resistance heating element or a Peltier element. Given employment of a Peltier element, it is also possible to cool the sensor array and the regulating electronics.

The resistance heating element can be fashioned in the form of a foil to be glued to whatever element it is mounted on. The foil can have a metallic conductor attached thereon. The metallic conductor is expediently a material having a relatively high resistance. Other suitable resistance materials can be employed instead of the metallic conductor. The heating element also can be provided with a temperature sensor. This can be a thermo-element. The thermo-element can be connected to a regulating device for regulating the temperature. An area occupied by the metallic conductor corresponds roughly to the area covered by the sensor array. The metallic conductor is fashioned with a serpentine shape so the surface is filled as uniformly as possible with the mechanical conductor.

The heating element can be glued onto a metal plate that is attached at the backside of the printed circuit board and that is preferably made of aluminum. The interposition of a metal plate between heating element and printed circuit board contributes to an especially uniform temperature flow to the sensor array. Temperature fluctuations which may be caused by the regulation are damped by the metal plate. Moreover, the provision of the metal plate contributes to shielding of the regulating electronics arranged behind the metal plate.

In a further embodiment, two recesses passing through the conductor plate and the metal plate are provided for the passage of fastening devices; enabling a simple fastening of the detector module. The fastening devices, for example screws, act on the metal plate, which has great rigidity; so that a durable and dependable fastening of the detector module can be achieved.

Expediently, the metallic conductor is connected via a cable to a plug that preferably has a snap-in catch. This enables a simple connection of the metallic conductor to a suitable bus. The catch opposes an unintentional release of the plug.

The sensor array can be a photodiode array, with interconnects for producing an electrical connection to the photodiode array being conducted in a flexible layer arrangement extending from the printed circuit board and proceeding to a further plug mounted at the free end of the layer arrangement. This arrangement enables a simple assembly of the detector module as well as a simple production of an electrical connection of the photodiode array to evaluation electronics.

The invention also is directed to a detector for an X-ray computed tomography apparatus having multiple inventive detector modules as described above arranged side-by-side.

The invention also is directed to a method for operating a computed tomography apparatus wherein each of the detector modules is heated to a prescribed temperature before the acquisition of the X-ray absorption distribution. The entire housing of the detector need no longer be heated with an unnecessarily high electrical power. The sensor arrays can be brought to the desired temperature faster. Further, it is possible to compensate a temperature gradient caused by different local heat elimination characteristics at the detector housing.

Advantageously, the heating elements of the detector modules are turned off during the acquisition of the X-ray absorption distribution. A disruption of the signals supplied by the sensor array that may possibly be caused by the operation of the heating elements thus is precluded.

In an embodiment of the method a first group of detector modules is heated to a first prescribed temperature and a second group of detector modules is heated to a second prescribed temperature. This makes it possible to compensate a previously determined temperature gradient at the detector housing. Further, the measured signal can be designationally influenced by the setting of different prescribed temperatures.

According to a further embodiment of the method, it is also possible to set the prescribed temperature using a calibration table stored for each of the detector modules. Such a setting leads to especially exact measured values. The temperature-dependent parameters that characterize the sensor elements are stored in the calibration tables. An individual compensation of each sensor array can ensue.

The activation and deactivation of the heating current, the setting of the prescribed heating temperatures or the regulation of the prescribed heating temperatures using the calibration data stored for each of the detector modules preferably can ensue program-controlled. Different heating modes can be prescribed by means of the program control.

DESCRIPTION OF THE PREFERRED EMBODIMENTS

Figure 1:
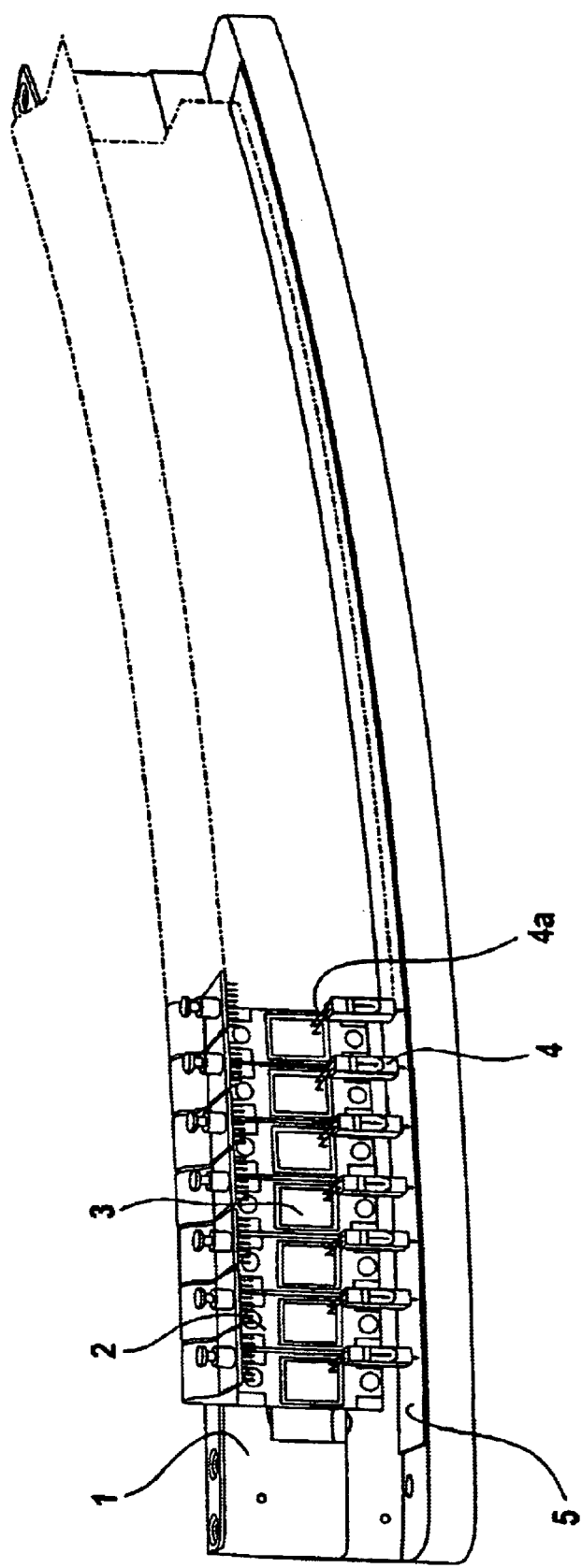
FIG. 1 is a perspective view of a detector in accordance with the invention.

FIG. 1 shows a detector for an X-ray computed tomography apparatus. Multiple first detector modules 2 are mounted side-by-side at a housing 1. A cable 4a extends from regulating electronics, the cable 4a being connected to a bus 5 by means of a plug 4.

Figure 2:
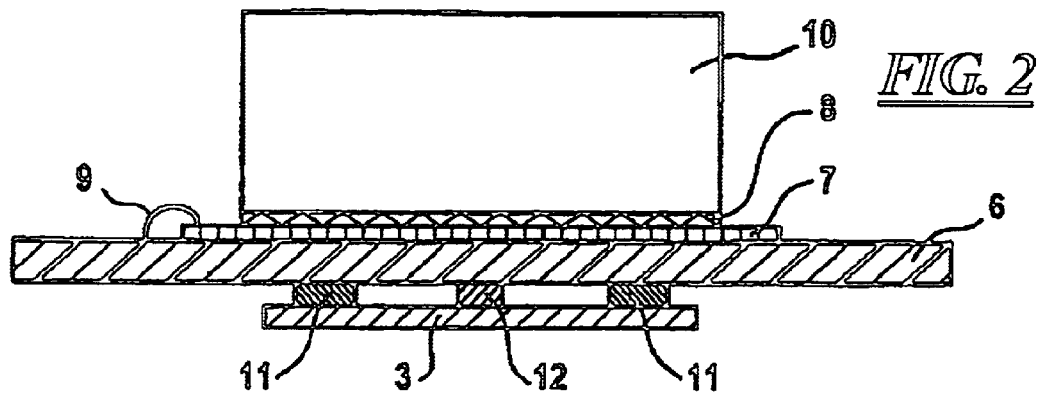
FIG. 2 is a schematic sectional view through a first detector module in accordance with the invention.
Figure 3:
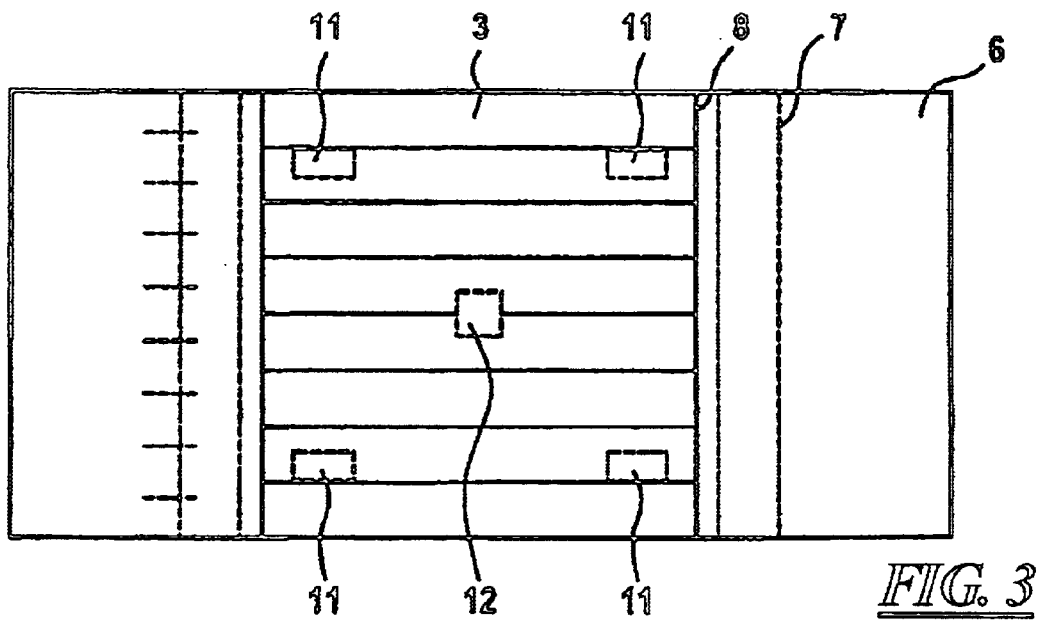
FIG. 3 is a plan view onto the backside of the detector module of FIG. 2.

The structure of the first detector module 2 is schematically shown again in FIGS. 2 and 3. A sensor array, formed of a photodiode array 7 and sensor elements 8 mounted thereon, is provided at a front side of a printed circuit board 6. The sensor elements 8 are expediently composed of a scintillator ceramic. They are glued onto the photodiode array 7. For electrical connection of the photodiode array 7, it is electrically conductively connected with a bond connection 9 to interconnects (not shown) provided on the printed circuit board. A collimator is referenced 10. A number of heating elements 11 are attached on the backside of the printed circuit board 6. A temperature sensor 12 is shown. The heating elements 11 can be resistance heating element or the like. The employment of Peltier elements is also possible. The temperature sensor 12 is expediently a thermo-element. The regulating electronics are arranged lying opposite the heating elements 11. A metal plate (not shown) can be provided between the heating elements 11 and the printed circuit board 6. A further metal plate (not shown) can be provided between the heating elements 11 and the regulating electronics 13. The provision of the metal plates serves for a compensation of temperature peaks as may occur in the regulation. The arrangement of the heating elements 11 and of the temperature sensor 12 is shown again in FIG. 3. It can also be seen from FIG. 3 that a total of eight sensor elements 11 arranged side-by-side are provided per detector module in this exemplary embodiment. The heating elements 11 are uniformly arranged in the corner regions of the area covered by the sensor array.

Figure 4:
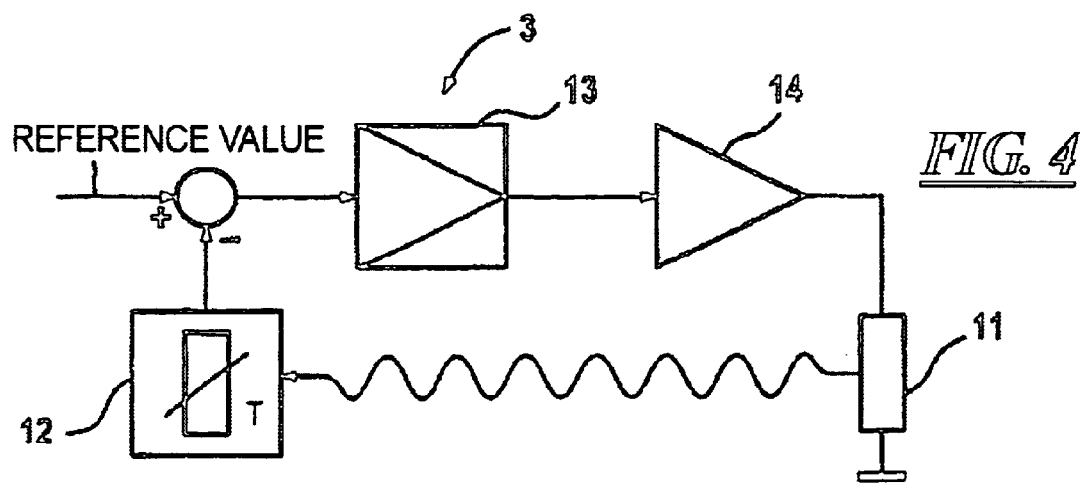
FIG. 4 is a schematic illustration of the basic components for regulating electronics. For a detector module in accordance with the invention.
Figure 5:
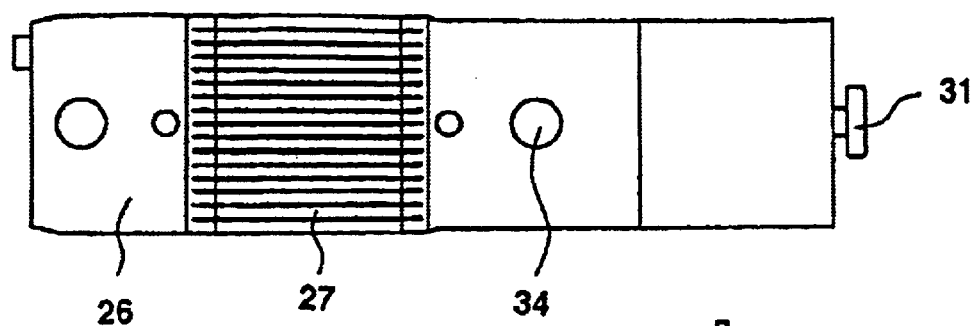
FIG. 5 is a plan view onto a second detector module in accordance with the invention.
Figure 6:
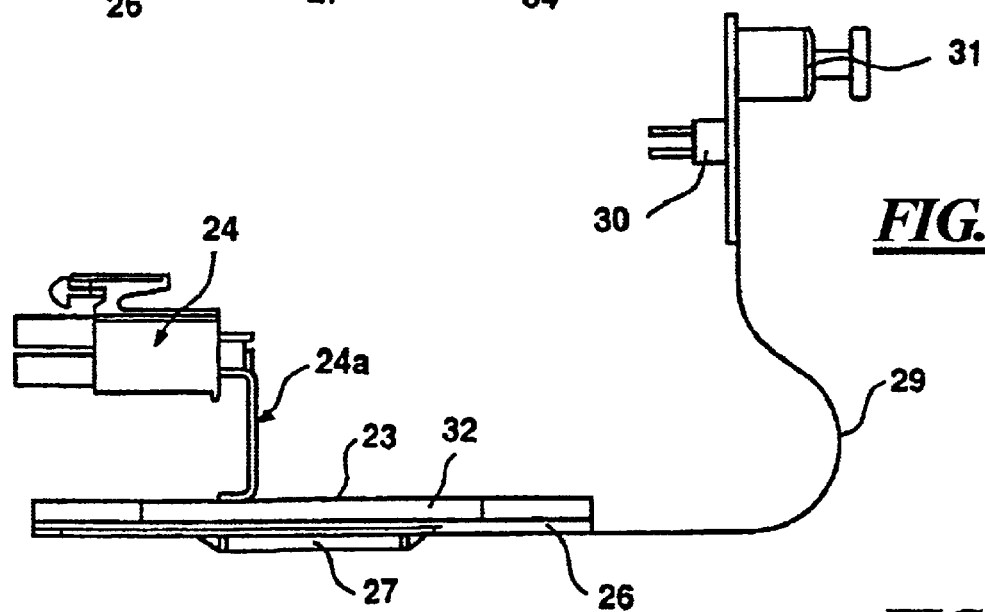
FIG. 6 is a side view of the detector module of FIG. 5.
Figure 7:
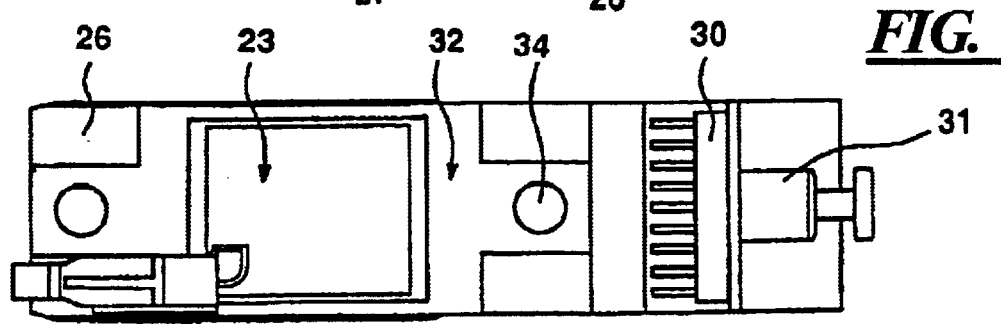
FIG. 7 is a bottom view of the detector module of FIG. 5.
Figure 8:
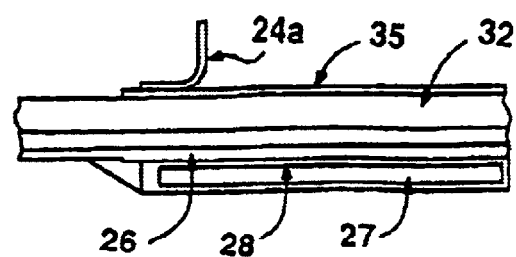
FIG. 8 is a detailed view according to FIG. 6.
Figure 9:
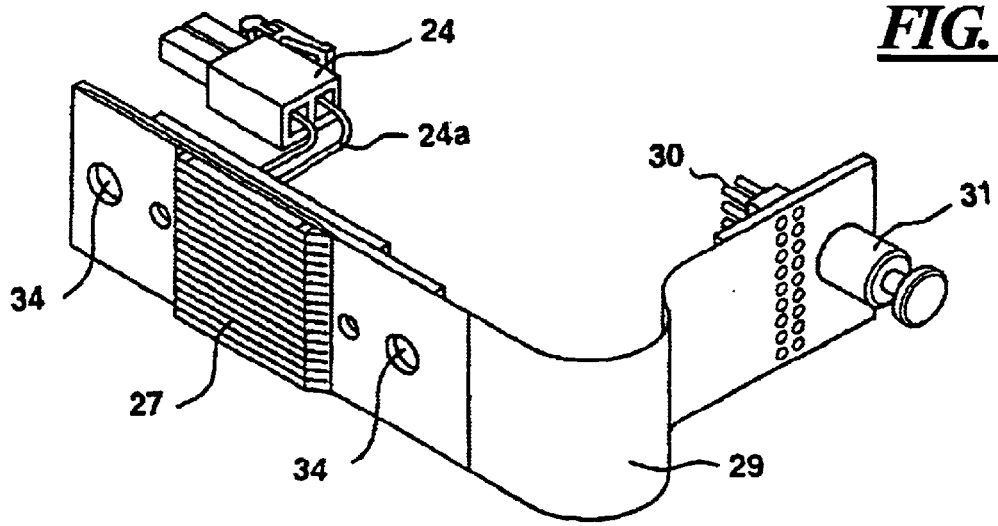
FIG. 9 is a first perspective view of the detector module of FIG. 5.
Figure 10:
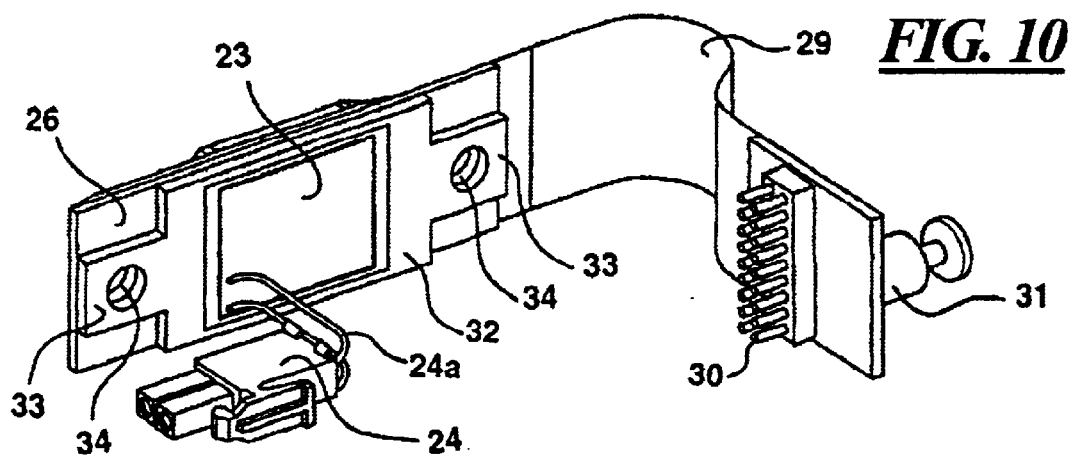
FIG. 10 is a second perspective view of the detector module of FIG. 5.
Figure 11:
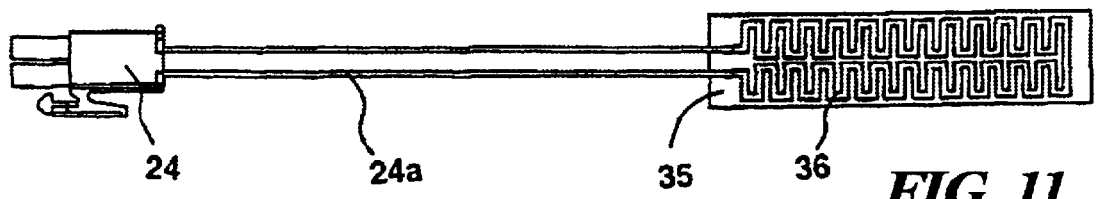
FIG. 11 is a plan view onto a foil with metallic conductor for a detector module in accordance with the invention.

FIG. 4 schematically shows the basic components of the regulating electronics 3, which include a proportional-integral regulator 13 and an amplifier 14.

Heat output by the heating element 11 is acquired by the temperature sensor 12 and is subsequently compared to a reference value. Using the proportional-integral regulator 13, the heating element 11 is suitably regulated via the amplifier 14 such that the reference value is established.

An advantage achieved due to the arrangement of the regulating electronics 3 in the proximity of the heating elements 11 (which can particularly be seen in FIG. 2) is that the temperature-dependency of the regulating electronics 3 is also compensated. An especially exact regulation of the temperature of the sensor array is achieved. This usually lies above room temperature and expediently amounts to approximately 30° C.

FIGS. 5 through 11 show the structure of a second inventive detector module in detail. A sensor array provided at a front side of a printed circuit board 26 has a number of sensor elements 27 arranged side-by-side that preferably are composed of a scintillator ceramic. The senor elements 27 are glued onto a photodiode array 28. The conductors or interconnects required for the electrical connection to the photodiode array 28 are conducted in a flexible section 29 extending from the printed circuit board 26, a further plug 30 for the connection to a following evaluation electronics being mounted at the end of said section 29. The flexible section 29 can be composed of a number of layers. These can be films made of polyimide between which interconnects are accepted. An interlock 31 assures that the further plug 30 does not come undone.

Lying opposite the sensor array, a metal plate 32 is glued on the backside of the printed circuit board 26. The metal plate 32 is expediently made of aluminum. Openings 34 that also extend through the printed circuit board 26 are provided in continuations 33 extending from the metal plate 32 at both sides. A foil 35 that carries the interconnects 36, and that is fashioned with a serpentine shape, is glued on the metal plate 32. A conventional adhesive or a double-sided adhesive film can be employed for gluing the foil 35. The foil 35 is expediently made of polyimide. The interconnects 36 are connected to a plug 24 via the cable 24a. The interconnects 36 are made of a metal having a high resistance, for example Konstantan or the like, that is suitable for heating purposes. The heating element 23 is designed such that the sensor array can be constantly held therewith at a temperature from approximately 30° C. through 35° C.

Although modifications and changes may be suggested by those skilled in the art, it is the intention of the inventors to embody within the patent warranted hereon all changes and modifications as reasonably and properly come within the scope of their contribution to the art.

We claim:

1. A detector for an X-ray computed tomography apparatus, comprising:
    a plurality of detector modules disposed side-by-side;
    each of said detector modules comprising a printed circuit board having a front side and a backside, a sensor array comprised of a plurality of sensor elements mounted at said front side of said printed circuit board, a metal plate glued to a backside of said printed circuit board facing away from said sensor array, and a resistance heating element for heating said sensor array comprising a foil sheet glued to said metal plate and having a metallic conductor applied thereon.

2. A detector module as claimed in claim 1 wherein said resistance heating element is disposed opposite said sensor array.

3. A detector as claimed in claim 1 wherein each of said detector modules further comprises regulating electronics attached to said printed circuit board for regulating said heating element.

4. A detector as claimed in claim 3, wherein said regulating electronics are fashioned as an integrated circuit.

5. A detector as claimed in claim 3 wherein each of said detector modules further comprises a temperature sensor attached to said printed circuit board and electrically connected to said regulating electronics.

6. A detector as claimed in claim 3 wherein said regulating electronics include a temperature sensor as a component of said regulating electronics.

7. A detector as claimed in claim 3 wherein said regulating electronics are disposed opposite said resistance heating element at a side thereof facing away from said printed circuit board.

8. A detector as claimed in claim 3 wherein the regulating electronics for the respective detector modules are individually operable for individually and separately regulating the respective heating elements of the respective detector modules.

9. A detector as claimed in claim 1 wherein said resistance heating element includes a temperature sensor.

10. A detector as claimed in claim 1 wherein said metallic conductor substantially fills an area corresponding to an area covered by said sensor array.

11. A detector as claimed in claim 1 wherein each detector module further comprises an electrical cable electrically connected to said heating element at a first end and terminating at a second end in a plug.

12. A detector as claimed in claim 11 wherein said plug comprises a snap-in catch.

13. A detector as claimed in claim 1 wherein said sensor array is a photodiode array having a plurality of electrical interconnects on said printed circuit board, and wherein each detector module further comprises a flexible flat cable electrically connected to said interconnects at a first end and terminating at a second end in a plug.

14. A method for operating an X-ray computed tomography apparatus comprising the steps of:
    disposing a plurality of X-ray detector modules side-by-side to form an X-ray detector;
    storing a calibration table for each of said detector modules representing temperature-dependent characteristics for the respective detector modules;
    providing each of said detector modules with an individually operable heating element and operating said heating elements to heat each of said detector modules to a prescribed temperature using the respective temperature-dependent characteristics stored in said calibration table; and
    after said detector modules are heated to said prescribed temperature, irradiating said radiation detector with X-rays at a plurality of irradiation angles and, at each irradiation angle, obtaining a dataset representing an X-ray absorption distribution at said X-ray detector, thereby obtaining a plurality of datasets, and forming an image of an examination subject, disposed preceding said radiation detector, from said datasets.

15. A method as claimed in claim 14 comprising discontinuing heating of said detector modules with said heating elements during irradiation of said X-ray detector with said X-rays.

16. A method as claimed in claim 14 comprising the additional step of dividing said detector modules into a first group of detector modules and a second group of detector modules, and wherein the step of heating said detector modules to said prescribed temperature comprises heating detector modules in said first group to a first prescribed temperature and heating detector modules in said second group to a second prescribed temperature.

* * * * *